(12) United States Patent
Nielsen

(10) Patent No.: US 6,924,892 B2
(45) Date of Patent: Aug. 2, 2005

(54) APPARATUS AND A METHOD OF INSPECTING PIECES OF CLOTH

(75) Inventor: Steen Nielsen, Brussels (BE)

(73) Assignee: Jensen Denmark A/S, Ronne (DK)

( * ) Notice: Subject to any disclaimer, the term of this patent is extended or adjusted under 35 U.S.C. 154(b) by 0 days.

(21) Appl. No.: 10/432,437

(22) PCT Filed: Oct. 9, 2001

(86) PCT No.: PCT/DK01/00657
§ 371 (c)(1),
(2), (4) Date: May 23, 2003

(87) PCT Pub. No.: WO02/42753
PCT Pub. Date: May 30, 2002

(65) Prior Publication Data
US 2004/0036866 A1 Feb. 26, 2004

(30) Foreign Application Priority Data
Nov. 27, 2000 (DK) .......................................... 2000 01784

(51) Int. Cl.$^7$ ............................................... G01N 21/00
(52) U.S. Cl. ............................... 356/238.1; 356/238.3; 356/430; 250/559.11
(58) Field of Search ........................... 356/238.1–238.3, 356/428; 250/428, 559.46, 223 R, 559.11; 382/111, 141

(56) References Cited

U.S. PATENT DOCUMENTS

| | | | |
|---|---|---|---|
| 4,057,351 A | | 11/1977 | Fomenko |
| 4,124,300 A | | 11/1978 | Mead et al. |
| 4,900,153 A | * | 2/1990 | Weber et al. ................ 356/430 |
| 4,953,400 A | * | 9/1990 | Bossuyt ........................ 73/159 |
| 5,068,799 A | * | 11/1991 | Jarrett, Jr. .................... 702/40 |
| 5,125,034 A | * | 6/1992 | Hudson et al. ............. 382/111 |
| 5,130,559 A | * | 7/1992 | Leifeld et al. ......... 250/559.11 |
| 5,224,172 A | * | 6/1993 | Masai ........................ 382/111 |
| 5,321,496 A | * | 6/1994 | Shofner et al. .......... 356/238.3 |
| 5,533,145 A | * | 7/1996 | Shofner et al. ............. 382/141 |
| 6,621,915 B1 | * | 9/2003 | Chen et al. ................. 382/111 |

FOREIGN PATENT DOCUMENTS

| | | |
|---|---|---|
| EP | 0676632 A2 | 10/1995 |
| GB | 2243847 A | 11/1991 |
| WO | WO99/10833 | 3/1999 |

* cited by examiner

Primary Examiner—Hoa Q. Pham
(74) Attorney, Agent, or Firm—Finnegan, Henderson, Farabow, Garrett & Dunner, L.L.P.

(57) ABSTRACT

A method and an apparatus for automatic inspection of flatly positioned pieces of cloth with a view to detecting impurities or other irregularities in pieces of cloth. The pieces of cloth are transported past a camera (10) that is, in cooperation with a digital storage unit, configured for producing a digital image of each piece of cloth or portions of each piece of cloth; and wherein the apparatus comprises one or more light emitters (11) with a view to illuminating at least that part of a piece of cloth that is within the field of vision of the camera (10). Each piece of cloth is conveyed from a receiver conveyor (12) to a delivery conveyor (13), the field of vision of the camera (1) being configured to have at least an open area (14) between these two conveyors (12, 13), whereby the digital image is recorded during the passage of a piece of cloth from the receiver conveyor (12) to the delivery conveyor (13).

11 Claims, 2 Drawing Sheets

APPARATUS AND A METHOD OF INSPECTING PIECES OF CLOTH

BACKGROUND OF THE INVENTION

The present invention relates to an apparatus for the automatic inspection of flatly positioned pieces of cloth with a view to detecting impurities or other irregularities therein and a method therefor.

By such methods and apparatuses it was previously known to convey each piece of cloth on the top side of a conveyor past a camera that is located above the conveyor and photographically records the piece of cloth from above. In those cases where the piece of cloth has just left a rotary ironer following preceding laundering, it is advantageous to inspect that side of the piece of cloth that had been facing the ironing side, since this is the most smooth side and hence the side on which impurities and irregularities will be most visible.

Such inspection from the ironing side has entailed that the pieces of cloth were to be turned before the inspection was carried out, which makes demands for both extra space and extra equipment. There is simultaneously a requirement, in special cases, for being able to inspect both sides of a piece of cloth, which also makes requirements for each piece of cloth being turned.

It is the object of the invention to provide a method and an apparatus that will, without need for additional space or equipment, enable inspection of the side of the pieces of cloth that has been facing the ironing side of a rotary ironer, and which enable inspection of both the one and the other or both sides of pieces of cloth.

SUMMARY OF THE INVENTION

This is obtained by an apparatus for automatic inspection of flatly positioned pieces of cloth with a view to detecting impurities or other irregularities; wherein the apparatus comprises means for transporting the pieces of cloth past a camera (10) that is, in cooperation with a digital storage unit, configured for producing a digital image of each piece of cloth or portions of each piece of cloth; and wherein the apparatus comprises one or more light emitters (11) with a view to illuminating at least that part of a piece of cloth that is within the field of vision of the camera (10), characterized in that the conveyance means comprises a receiver conveyor (12) and a delivery conveyor (13), the field of vision of the camera (1) being configured for comprising at least an open area (14) between these two conveyors (12, 13), whereby the digital image is recorded during the passage of a piece of cloth from the receiver conveyor (12) to the delivery conveyor (13).

A method is also provided for automatic inspection of flatly positioned pieces of cloth with a view to detecting impurities or other irregularities; wherein the pieces of cloth are transported past a camera (10) that is, in cooperation with a digital storage unit, configured for producing a digital image of each piece of cloth or portions of each piece of cloth; and wherein the apparatus comprises one or more light emitters (11) with a view to illuminating at least that part of a piece of cloth that is within the field of vision of the camera (10), characterized in that each piece of cloth is transferred from a receiver conveyor (12) to a delivery conveyor (13), the field of vision of the camera (10) being configured for comprising at least an open area (14) between these two conveyors (12, 13), whereby the digital image is recorded during the passage of a piece of cloth from the receiver conveyor (12) to the delivery conveyor (13).

By allowing the pieces of cloth to pass an open area between two conveyors, it becomes possible to inspect the piece of cloth from either the one or the other side in the open area between the conveyors. Thus it is possible to inspect a piece of cloth from the side that faces towards the ironing side after the piece of cloth has left a rotary ironer, even in case it is the side that faces towards the receiver conveyor due to the fact that the inspection takes place in an open area between the receiver conveyor and the delivery conveyor. Thus, the recording of the digital images that is a prerequisite for the inspection to take place from the side(s) that is/are most appropriate in the relevant situation.

It will be possible herein to configure the receiver conveyor at a higher level than the delivery conveyor, whereby the passage from the one to the other conveyor is accomplished substantially vertically and such that the inspection is accomplished in accordance with a substantially horizontal line of sight. However, this is associated with certain difficulties during the passage of the end of the pieces of cloth that will have a propensity to drop down onto the delivery conveyor when an end portion of the piece of cloth reaches the end of the receiver conveyor.

It is therefore preferred that the delivery conveyor and the receiver conveyor are located essentially flush with each other, the inspection being performed along a line of sight that is substantially perpendicular to the two preferably horizontally extending conveyors.

There is located between the camera and the area between the two conveyors a transparent cover. Hereby a physical barrier is obtained that is able to separate the very sensitive electronics in the camera from the pieces of cloth. This is particularly important in laundries where the pieces of cloth come from a rotary ironer and thus emit both heat and moisture that may adversely influence the camera and the light emitters. Conveniently the covering is configured as a glass board.

The receiver conveyor and the delivery conveyor being located essentially in extension of each other and configured for conveying the piece of cloth slidingly across the transparent cover between them, it is obtained that the transparent cover is continuously cleaned of deposits, if any, in the form of fluff or other impurities.

Advantageously the transparent cover forms a window in a closed container, in which the camera is located. Hereby it is possible to monitor accurately the climate in which the camera is situated such that constant temperature and humidity can be maintained. Thereby optimal and constant conditions of operation for the camera are ensured. The width of the pieces of cloth that are to be photographed by the camera being considerable, a mirror arrangement is conventionally used that provides an optical distance between the camera and the pieces of cloth that is close to the maximal width, and by positioning these mirrors in the closed container, the mirrors are safeguarded against deposits of particles and fluff that might otherwise adversely affect the quality of the images recorded.

Advantageously, the light emitters are arranged between the camera and the transparent cover, due to the fact that the transparent cover thereby also protects the light emitters. The light emitters can conveniently be arranged in the closed container. Of course it is also possible to arrange one or more light emitters opposite the transparent cover, and in that case the camera will record an image that derives at least partially from light transmitted through the pieces of cloth.

Advantageously a light emitter is configured as an elongate light guide arranged transversally to the two conveyors along the area located there between, and such that the light guide is supplied with light at one or both ends, and wherein the light guide is configured for emitting light along the longitudinal axis of the light guide.

Light emitters of this type are known, but herein the particular advantage is obtained that the strongly heat-emitting light source can be arranged at a suitable distance from the camera and in a place where it is easy to provide for a suitable cooling. In previously known apparatuses for this type of inspection, fluorescent tubes, such as eg neon tubes were used, but it has been found to be difficult to obtain an entirely uniform illumination over the width that is required in case of laundry machines, and besides the replacement of burnt-out neon tubes have required more protracted operation halts with ensuing adverse effects on the production. Finally it is necessary to locate the fluorescent tubes quite close to the pieces of cloth, which has resulted in a heating of the pipes with ensuring variations in the light emission. Further it should be noted that light guides are considerably less space-consuming than fluorescent tubes, which makes it possible to keep the open space between the two conveyors suitably narrow, whereby the distance to be travelled by the piece of cloth without being supported by a conveyor is limited as much as possible.

A convenient configuration of the light guides is obtained in case they each comprise a glass rod that has, along its longitudinal axis, dispersion means for causing the light to leave the glass rod along the longitudinal axis. A suitable dispersion means could in this case be constituted of one or more ground facets distributed along the longitudinal axis of the rod. The ground surface(s) of a facet will disperse the light and thus the dispersed light will hit the surface of the glass rod at an angle that allows the light to leave the rod. Conveniently rods of quartz glass are used that are transparent to a light over a wide wavelength area.

Use of light guides of the above-mentioned type makes it particularly simple to insert filters at the end of each rod between the rod and the light source. Thus, the spectral composition of the light can be regulated in accordance with the type of laundry to be inspected. Replacement of burnt-out bulbs in the light source can be carried out in a readily accessible spot at a side portion outside the closed container, and thus replacement of bulbs becomes possible without considerable operational disturbances.

It is preferred to use light with a mixture of wavelengths in the ultraviolet range and the blue-violet range.

Now follows a detailed explanation of an exemplary, concrete embodiment of the invention with reference to the figures of the drawing, wherein

DETAILED DESCRIPTION OF THE INVENTION

Figure 1:
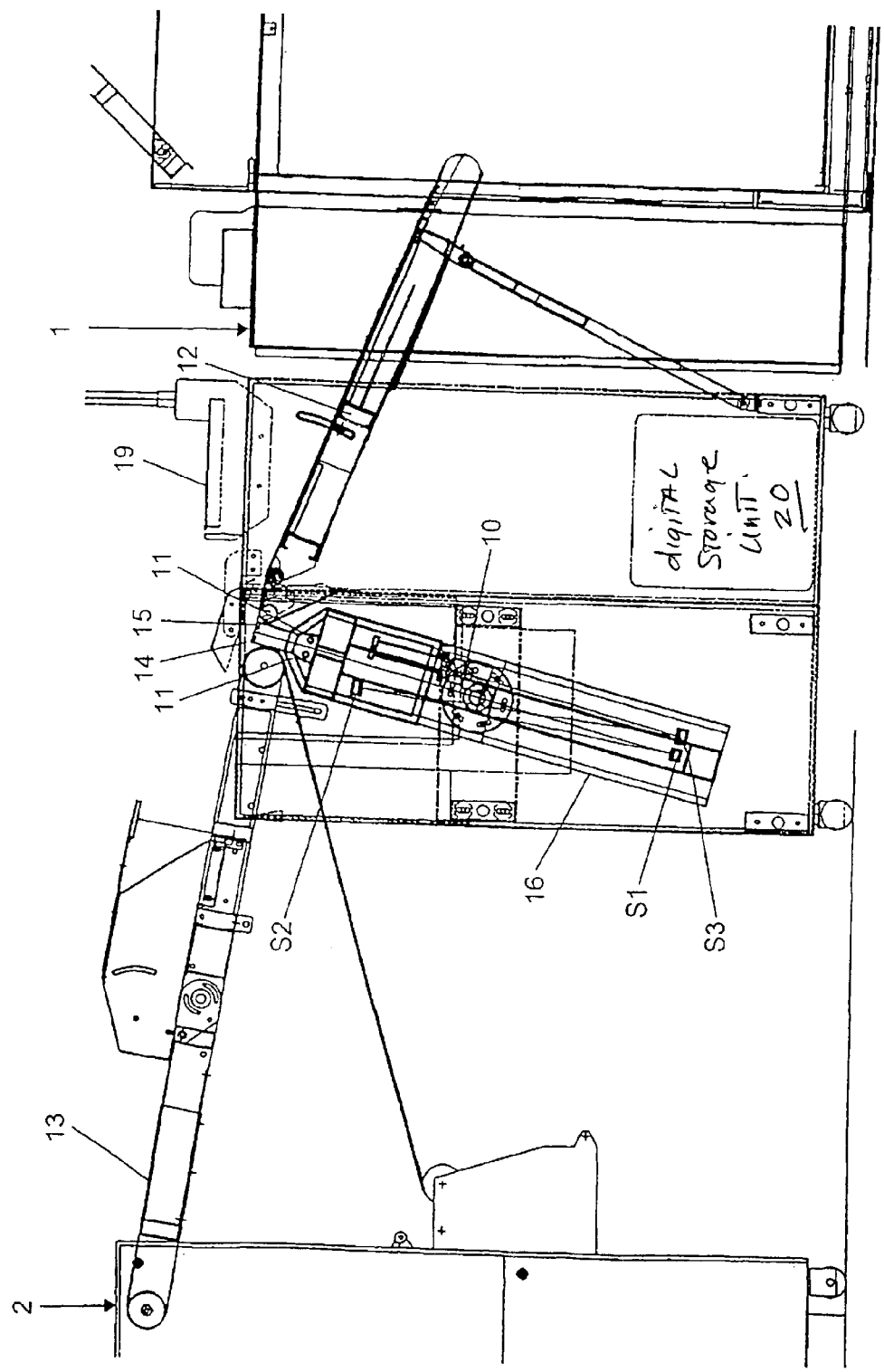
FIG. 1 shows a lateral view of a rollway, comprising a rotary ironer, an inspection apparatus according to the invention and a folding machine.

FIG. 1 shows a common rotary ironer 1, to the outlet end of which there is coupled a receiver conveyor 12. The pieces of cloth are conveyed from the receiver conveyor 12 onto a delivery conveyor 13 and from there the pieces of cloth are delivered to, e.g. a folding machine 2 that folds the pieces of cloth. Between the receiver conveyor 12 and the delivery conveyor 13 there is an open space 14, where the pieces of cloth are not supported by a conveyor. Underneath the open area there is located a camera 10 that is, via a number of mirrors S1, S2 and S3, configured for photographing the area 14 between the two conveyors.

In the example shown in FIG. 1 the receiver and delivery conveyors follow each other at approximately the same level, but it is also an option to configure the delivery conveyor 12 at a level below the receiver conveyor 13, whereby the pieces of cloth will, during the transfer between the conveyors, be freely suspended, and then to configure the camera 10 with a substantially horizontal line of sight. Hereby the same advantage could be obtained, viz that the camera 10 can be configured to watch any of the two sides of the piece of cloth.

As shown in FIG. 1 and in the current example, the camera 10 is located underneath the open area between the conveyors 12, 13 and thus the camera 10 will record an image of that side of the piece of cloth that has faced towards the ironing side of the rotary ironer 1. This is a considerable advantage over previous systems, since the ironing side is the most smooth, and the side where discolourations, if any, that were not removed during the preceding laundering procedure are most visible.

In the area 14 between the two conveyors 12,13 there is arranged a transparent cover plate 15 that serves several purposes. It supports the piece of cloth between the two conveyors, and in this context it has surprisingly been found that it is possible, without any problems whatsoever, to push the front end of a piece of cloth transversally across the cover plate 15 without folds occurring in the piece of cloth. The cover plate 15 also contributes to making a physical shield for the camera 10. This is important, since—during passage of the apparatus—the pieces of cloth will emit both a certain amount of heat and some degree of moisture, which may adversely influence the operational stability of the camera 10.

For the same reason the cover plate 15 forms a window in a container 16, in which the camera 10 is located along with the associated mirror arrangement. Thereby it is possible to maintain a constant climate around the camera 10. Simultaneously it is ensured that fluff and other impurities, which are unavoidable in the surroundings of a laundry, are not deposited on the mirrors.

Figure 2:
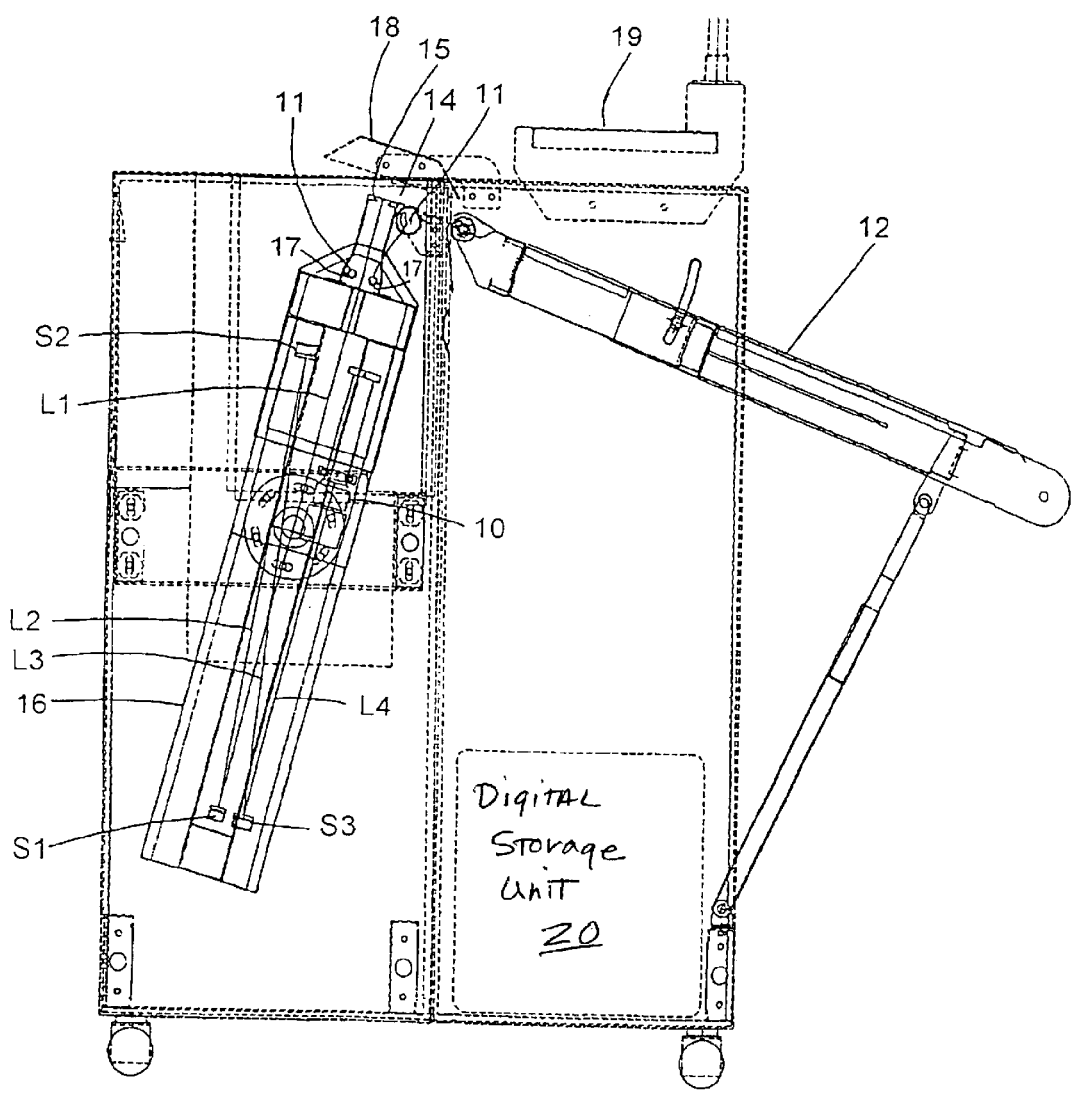
FIG. 2 is an enlarged sectional view of FIG. 1 and shows the inspection apparatus in combination with the receiver conveyor.

FIG. 2 is an enlarged reproduction of the container 16 as such with the camera 10. The travelling of the light from the underside of a piece of cloth to the camera is also shown herein. The travelling of the light from the underside of the glass plate 15 via the mirrors S1, S2, S3 and further on to the camera 10 is shown by lines L1, L2, L3 and L4.

Glass rods 11 are located each in their holder, and at the end of each rod, lights sources are provided that are not shown in the figure. The light sources are commercially available sources that emit light in a desired spectral area. In the embodiment shown in FIGS. 1 and 2, the rods 11 are located to each side of the line L1, and thereby symmetrical illumination of the piece of cloth across the glass plate is obtained and the advantage of this is that folds, if any, generated during the ironing process do not entail shadow formation that could be interpreted as impurities in the piece of cloth. If a sufficiently strong light source is used, however, a rod will often be sufficient, which is financially advantageous.

This type of light emitters is associated with the problem that the light intensity has a propensity to decrease with increasing distance from the light source, and that the light will have a propensity to leave the rod at a relatively acute angel relative to the longitudinal axis of the rod. It has been attempted to solve these problems by grinding a number of discrete facets in the rod surface, whereby the ground surface of each facet will serve as diffusion face. Variations in the distance between the facets enable a more even emission of light along the longitudinal axis of the rod, and selection of the angle between the surface of the facets and the longitudinal axis of the rod serves to ensure that the light leaves the rod at an angle that is rather close to 90°. By these measures it is possible to achieve uniform emission of light along the entire expanse of the rod and at an angle that does not presuppose a length of the rod that does not considerably exceed the width of the conveyors.

The area of the glass plate 15 and that of the piece of cloth that is to be illuminated need not have a width of more than about 2 mm for the sake of the camera. To obtain a high light intensity, it may be advantageous to position an optical lens between the glass rod 11 and the plate 15. Hereby the light emitted from the rod can be focused in a narrower area and hence a higher light intensity is accomplished. Likewise, a focusing effect can be obtained by selecting glass rods that do not feature circular cross-sections as shown; they rather have a cross section that comprises two straight parallel sides and two circular arches that connect each of the two sides. In this context facets are ground in the one circular arch and the light will then leave by the opposite arch.

It is preferred to use a light source that emits light within the spectral range of from 350 nm to 500 nm. Albeit the lower portion of this interval is not visible to the camera, the addition of optical whitener to the laundry detergents will enable that the light received by the pieces of cloth within the lower spectral range will be reflected within the visible area around 450 nm. Hereby a marked improvement is obtained of the contrast between clean and not clean portions of the piece of cloth, due to the not-clean areas having a propensity to block the effect of the contents of optical whitener of the piece of cloth.

In the area above the glass plate 15, a cap 18 is provided that prevents light conditions prevailing in the surrounding environment from influencing the illumination of the piece of cloth.

Advantageously the glass plate 15 can be located at a level that is slightly above the level for the receiver and delivery conveyors in order to thereby ensure that each piece of cloth is caused to slide across the glass plate. Thereby the glass plate is continuously kept clean which is an essential prerequisite for successful photographing of the piece of cloth.

A usual gangway 19 is provided in the area above one of the conveyors.

In a known manner the camera is configured for recording one line at a time in the transverse orientation of the piece of cloth and by collecting the lines, an overall image is obtained in a conventional manner of what passes by on the glass plate 15. In a digital storage unit or a conventional computer 20 this overall image is recorded and analysed; in the first instance to separate the individual pieces of cloth from the surroundings, and subsequently to subject the image of each piece of cloth to an analysis to detect impurities, spots or defects in the fabric; and on the basis of the result a signal is emitted to the folding machine 2 to which destination the piece of cloth in question is to be sorted to go to.

It will be possible within the framework of the system to also apply a bar code to each piece of cloth, which bar code is decoded by the analysis of the image of the piece of cloth and that identifies each piece of cloth. Use of suitable wavelengths of the illumination will also enable such configuration of a bar code that it is more or less invisible to the eye, but readily readable to the camera.

The two conveyors 12 and 13 can be independent units, or they can be integral parts of the rotary ironer and the folder, respectively.

What is claimed is:

1. An apparatus for the automatic inspection of flatly positioned pieces of cloth for detecting impurities or other irregularities therein, said apparatus comprising means for transporting the pieces of cloth past a camera that is, in cooperation with a digital storage unit, configured for producing a digital image of each piece of cloth or portions of each piece of cloth, one or more light emitters for illuminating at least that part of a piece of cloth that is within a field of vision of the camera, wherein the conveyance transporting means comprises a receiver conveyor and a delivery conveyor, the field of vision of the camera being located at least in an open area between these two conveyors and a transparent cover located between the camera and the open area between the two conveyors, whereby a digital image is recorded during the passage of a piece of cloth from the receiver conveyor to the delivery conveyor.

2. The apparatus according to claim 1, wherein the receiver conveyor and the delivery conveyor follow essentially in extension of each other and are configured for conveying the piece of cloth slidingly across the transparent cover.

3. The apparatus according to claim 2, wherein the transparent cover forms a window in a closed container in which the camera is located.

4. The apparatus according to claim 3, wherein the one or more light emitters are arranged between the camera and the transparent cover.

5. The apparatus according to any one of claims 1, 2 or 3, wherein at least one light emitter is an elongated light guide that is arranged transversally to the two conveyors in the open area and wherein the light guide is supplied with light at one or both ends thereof and emits light along its longitudinal axis.

6. The apparatus according to claim 5, wherein each light guide comprises a glass rod that has, along its longitudinal axis, dispersion means for causing the light to leave the glass rod along its longitudinal axis.

7. A method for the automatic inspection of flatly positioned pieces of cloth with a view to detecting impurities or other irregularities therein, said method comprising the steps of transporting pieces of cloth past a camera that is, in cooperation with a digital storage unit, configured for producing a digital image of each piece of cloth or portions of each piece of cloth illuminating with one or more light emitters at least that part of a piece of cloth that is within a field of vision of the camera, each piece of cloth being transferred from a receiver conveyor to a delivery conveyor past the field of vision of the camera located at least in an open area between these two conveyors and over a transparent cover located in the open area between the two conveyors and between the piece of cloth and the camera and recording a digital image during the passage of a piece of cloth from the receiver conveyor to the delivery conveyor.

8. The method according to claim 7, wherein the receiver conveyor and the delivery conveyor convey the piece of cloth slidingly across the transparent cover.

9. The method according to claim 8, wherein the transparent cover forms a window in a closed container in which the camera is located.

10. The method according to claim 9, wherein the container is located underneath the two conveyors.

11. The method according to claim 7, wherein the receiver conveyor receives pieces of cloth from a rotary ironer and the delivery conveyor delivers the pieces of cloth to a folding machine that has two or more destination options for a folded piece of cloth, wherein the relevant destination is determined by analysis of the recorded digital image of the piece of cloth.

* * * * *